(12) United States Patent
Olbertz

(10) Patent No.: US 7,587,244 B2
(45) Date of Patent: Sep. 8, 2009

(54) SPRING CONTACT ELEMENT

(75) Inventor: Ralf Olbertz, Berlin (DE)

(73) Assignee: Biotronik GmbH & Co. KG (DE)

( * ) Notice: Subject to any disclaimer, the term of this patent is extended or adjusted under 35 U.S.C. 154(b) by 448 days.

(21) Appl. No.: 11/099,064

(22) Filed: Apr. 5, 2005

(65) Prior Publication Data
US 2006/0004419 A1    Jan. 5, 2006

(30) Foreign Application Priority Data
Apr. 5, 2004    (DE) .................. 10 2004 017 659

(51) Int. Cl.
*A61N 1/375* (2006.01)
(52) U.S. Cl. ...................................... 607/37
(58) Field of Classification Search .............. 607/36, 607/37
See application file for complete search history.

(56) References Cited

U.S. PATENT DOCUMENTS

| | | | |
|---|---|---|---|
| 3,678,445 A | 7/1972 | Brancaleone | |
| 4,106,839 A | 8/1978 | Cooper | |
| 4,423,919 A | 1/1984 | Hillis | |
| 4,426,127 A | 1/1984 | Kubota | |
| 5,275,620 A | 1/1994 | Darby et al. | |
| 5,730,628 A | 3/1998 | Hawkins | |
| 7,003,351 B2 * | 2/2006 | Tvaska et al. ............ | 607/37 |
| 7,164,951 B2 * | 1/2007 | Ries et al. ............... | 607/37 |
| 2004/0167582 A1 | 8/2004 | Tvaska et al. | |
| 2005/0107859 A1 * | 5/2005 | Daglow et al. ........... | 607/116 |

FOREIGN PATENT DOCUMENTS

| | | |
|---|---|---|
| DE | 196 09 367 A1 | 9/1997 |
| EP | 0 590 756 A2 | 4/1994 |
| EP | 0 840 400 A2 | 5/1998 |
| EP | 0 848 584 A1 | 6/1998 |
| EP | 1 107 377 A1 | 6/2001 |

* cited by examiner

*Primary Examiner*—George R Evanisko
*Assistant Examiner*—Amanda Patton
(74) *Attorney, Agent, or Firm*—Hahn Loeser & Parks LLP

(57) ABSTRACT

A contact arrangement for connecting an electrode line to an implantable device, comprises an electrical connecting socket with a socket longitudinal axis and at least one opening for the insertion of a plug along the socket longitudinal axis. The arrangement includes at least one electrically conductive spring contact element, arranged and adapted to deflect resiliently elastically outwardly upon insertion of a plug, by compression in a spring deflection direction extending transversely with respect to the socket longitudinal axis and providing a spring force acting in opposition to the compression. The arrangement has a spring contact element with an integral metallic spring contact tongue, with spring contact tongue portions which extend transversely with respect to the spring deflection direction and which are connected together by turn portions. The turn portions occurring in immediate succession in the spring deflection direction are turned towards each other with respectively opposite turn directions.

10 Claims, 3 Drawing Sheets

SPRING CONTACT ELEMENT

BACKGROUND OF THE INVENTION

The invention concerns a contact arrangement for connecting an electrode line to an implantable device. The contact arrangement has an electrical connecting socket with a socket longitudinal axis and at least one opening for the insertion of a plug along the socket longitudinal axis. The contact arrangement also has at least one electrically conductive spring contact element which is arranged and adapted to deflect resiliently elastically outwardly upon insertion of a plug, in that case to be compressed at least in a spring deflection direction extending transversely with respect to the socket longitudinal axis and to provide a spring force acting in opposition to the compression.

Spring contact elements for implantable devices are known from the state of the art. DE 196 09 367 to the present applicants discloses a cardiac pacemaker having a sleeve of a round configuration for receiving an electrode line, having radially inwardly resilient spring contact elements which are distributed uniformly at the periphery of the sleeve. The spring contact elements are of a strip-shaped configuration; they are fixed at one side to the sleeve wall and they face into the space in the sleeve, wherein the free end thereof is of a hemispherically convex configuration and faces with the convex side radially inwardly.

Such spring contact elements suffer from the problem that the contact spring pressure force can only be adjusted with difficulty, in particular, if—as is often usual—the spring element is stamped out of the sleeve wall and the leaf spring obtained in that way is bent into the interior of the sleeve. Here there is a reliance in terms of the choice of material for making the spring on the sleeve material so that, in such a case, there is always a compromise between demands on a sleeve and the demands on a contact spring for making secure good electrical operative contact with an electrode line.

BRIEF SUMMARY OF THE INVENTION

Therefore an aspect of the invention is to provide a contact element which permits reliable galvanic contact with an electrode line plug.

That aspect is attained by a contact arrangement having a connecting socket for an implantable device of the kind set forth in the opening part of this specification, wherein the spring contact element has an integral metallic spring contact tongue with spring contact tongue portions which extend transversely with respect to the spring deflection direction and which are connected together by turn portions, wherein turn portions which occur in immediate succession in the spring deflection direction are turned towards each other with respectively opposite turn directions.

In a preferred embodiment, the spring contact element has a spring contact tongue. The spring contact tongue is turned in such a way that in a plan view on to a plane defined by the socket longitudinal axis and the spring deflection direction, the spring contact tongue is of a wave shape.

In the case of a wave-shaped spring contact element with two or more turn portions, a spring contact element can be constructed to particular advantage with a soft spring stiffness in the spring deflection direction. A further advantage of such a spring contact element is that the spring stiffness is easily adjustable in the spring direction.

The wave shape of the spring contact element can be an S-shaped, a rectangular or a triangular wave shape. Due to the design configuration of the spring contact element in accordance with various wave shapes, the spring contact element, depending on the respective wave shape selected, involves differing spring stiffness, in particular in dependence on a spring deflection caused by the compression effect. In that way, a desired spring stiffness can be advantageously set, by way of the choice of the wave shape.

In a preferred embodiment, the spring contact element has three or four turn portions, so that the wave shape of the spring contact element includes three or four half-waves. A spring contact element can afford a particularly soft spring stiffness by virtue of the series connection achieved in that way of spring contact elements respectively formed by turn portions.

In a preferred embodiment, the spring contact tongue of the spring contact element is a turned leaf spring. The leaf spring has a leaf spring cross-sectional profile whose width dimension is greater than its height dimension. By virtue of being in the form of a turned leaf spring, the spring contact element has a high level of torsional stability in tangential relationship with the spring deflection direction. In the situation of use, a spring contact element cannot be bent so easily if an electrode line plug is not introduced into the electrode line connecting socket precisely parallel to the socket longitudinal axis.

Preferably, the width dimension of the leaf spring cross-section is five times the height dimension of the leaf spring cross-section.

In an alternative embodiment, the spring contact tongue can be of a square or round cross-section.

In a preferred embodiment, the arrangement has at least three spring contact elements, wherein the spring deflection directions of the spring contact elements are arranged in a common plane extending perpendicularly to the socket longitudinal axis.

By virtue of that arrangement, a ring contact of an electrode line plug can be touched in the situation of use by a plurality of spring contact elements so that this affords a high degree of contact certainty, linked to a low level of electrical contact transfer resistance.

In a preferred embodiment, a contact portion of the spring contact tongue has a surface region which is provided for making contact with a counterpart contact of an electrode line plug and which is convexly shaped. In the situation of use, that advantageously facilitates the insertion of an electrode line plug into the electrode line connecting socket.

Advantageous embodiments of a spring contact tongue have one or a combination of the following materials:

High-alloyed steels in accordance with DIN 17224; X 12 CrNi 17 7; X 7 CeNiAl 17 7; or X 5 CrNiMo 18 10 or other high-alloyed metal alloys.

A spring contact tongue can advantageously be at least portion-wise silver-plated, gold-plated, coated with platinum bromide (PtBr) or may have a combination of such coatings. By way of example a spring contact tongue is copper-plated and silver-plated thereover.

In another embodiment, the spring contact element has at least one elastomer element which at least partially fills an intermediate space which extends between two leaf spring portions disposed in opposite relationship in the spring deflection direction, wherein the elastomer material is designed and arranged as a deflection travel limiting means.

That advantageously prevents plastic deformation of the spring contact element, caused by an excessively large deflection movement. By way of example, the elastomer element is a silicone elastomer element which contains a silicone rubber.

In a preferred embodiment, the elastomer element is so shaped that it fills the intermediate space partially and preferably as far as half in the deflection direction.

In another embodiment, the elastomer element is shaped to completely fill the intermediate space, wherein the elastomer element material is of a modulus of elasticity which is so selected that the elastomer element does not substantially increase the overall spring stiffness of the spring contact element along the spring deflection direction.

Preferably, the modulus of elasticity of the elastomer element is so selected that the overall spring stiffness of the spring contact element is not increased by more than 5% in comparison with a spring stiffness of a spring contact element without an elastomer element.

In an advantageous embodiment, the elastomer element is so shaped that it completely surrounds the spring contact element except for a portion provided for electrical contacting purposes. In that embodiment, the spring contact element is advantageously protected from moisture, corrosion and plastic deformation.

In a preferred embodiment, a spring contact element arrangement for a contact arrangement has a spring contact element carrier with at least three, and preferably four, and further preferably six, spring contact elements formed thereon. The spring contact element carrier in the form of a round flat disk having an aperture—preferably arranged centrally—to pass therethrough.

In a further preferred embodiment, the spring contact elements are arranged on the spring contact element carrier uniformly in the peripheral direction and are arranged in the region of the outer edge of the spring contact element carrier.

The spring contact elements are particularly preferably each formed from a respective leaf spring tongue turned in a wave shape, wherein the leaf spring tongue has two turn portions with respective mutually opposite turn directions and is thus of an S-shaped wave shape. The leaf spring tongues are adapted, with deflection along a spring deflection axis, to provide a spring force opposing the deflection, and upon insertion of a plug, to deflect resiliently elastically outwardly.

In an advantageous variant, the spring contact element carrier has recess regions respectively laterally adjoining the spring contact elements, in the peripheral direction.

In a further preferred feature, the spring contact element carrier has recess regions respectively arranged in opposite relationship to each spring contact element in the peripheral direction at the inner edge which adjoins the aperture through the spring contact element. The recesses at the inner edge of the spring contact element carrier towards the aperture are preferably cut outwardly in the radial direction to such a depth that a region which still occurs there of the spring contact element carrier between the outer and the inner recesses—as viewed in the radial direction—forms a torsion spring which is operative in a tangential direction. The torsion spring acts in series with the spring contact elements and advantageously facilitates insertion of a plug into a connecting socket.

In a preferred variant, the spring contact element carrier with the spring contact elements is formed from an integral metal sheet which has leaf spring strips facing radially outwardly in a radiating configuration. The spring contact elements are respectively formed from the leaf spring strips facing radially outwardly in a radiating configuration, wherein the leaf spring strips are angled—preferably at a right angle—at the peripheral attachment of the spring contact element carrier and are shaped in the further course thereof to provide an S-shaped wave shape.

The spring contact element carrier with the spring contact elements can be stamped or laser-cut out of a metal sheet.

In an advantageous embodiment, the recesses are cut laterally of the spring contact elements in a radial direction to such a depth that, after a leaf spring strip is angled at least through a right angle, a portion of the leaf spring strip, beginning at the periphery of the spring contact element carrier (215), does not exceed an outer peripheral radius of the spring contact element carrier (215) beside the recesses.

In a preferred embodiment, the arrangement also includes a sleeve with a sleeve longitudinal axis and a sleeve wall. The sleeve wall encloses an internal sleeve space which has at least one opening for the insertion of an electrode plug in the direction of the sleeve longitudinal axis.

In the embodiment described herein, the sleeve longitudinal axis and the socket longitudinal axis of the connecting socket are in mutually parallel relationship or form a common axis. The spring contact element can be at least partially arranged in the internal space of the sleeve.

In an embodiment, the sleeve wall has an aperture for receiving a spring contact element, the spring contact element being arranged in the aperture in such a way that at least one portion of the spring contact element, which is provided for electrically contacting an electrode line plug, is arranged in the internal space of the sleeve.

In a particularly preferred embodiment, the sleeve wall is of a cylindrical configuration and the internal space of the sleeve, in the direction of the sleeve longitudinal axis, has two openings for receiving an electrode plug so that the sleeve is completely pierced in the direction of the sleeve longitudinal axis. The sleeve wall can also be of a semicircular, rectangular or square cross-section.

In a further preferred feature, the sleeve has at least three, particularly preferably six, spring contact elements, the spring contact elements being arranged in a common plane extending perpendicularly to the sleeve longitudinal axis.

In another embodiment, the sleeve includes a seal which has a round aperture for receiving an electrode line and which is shaped in such a way as to seal off the opening in relation to the sleeve wall and in relation to the aperture—and thus in the situation of use in relation to an electrode line. Preferably the aperture is of a round cross-section. In that way, spring contact elements are effectively protected from the ingress of body fluid and thus also from corrosion.

The advantageous combination of a sealing disk with a spring contact element carrier having inwardly projecting spring contact elements which are arranged within a common sleeve in succession in the longitudinal direction of the sleeve represents an independent idea of the invention.

In a further preferred feature, a seal is a sealing disk having an aperture with an aperture internal wall, wherein the aperture internal wall has at least two sealing lips which are arranged in succession in the sleeve longitudinal axis and which each face radially inwardly—and thus in the direction of the socket longitudinal axis and which are formed on the sealing disk. The sealing lips jointly afford a particularly good sealing action, in particular if the sealing action of a sealing lip is lost, for example due to damage or irregularities on an electrode line inserted into the connecting socket.

The sealing disk is preferably so arranged that the sleeve longitudinal axis extends perpendicularly to the plane of the sealing disk.

In a further preferred feature, the sealing disk is formed on the sleeve. In a preferred embodiment, in the region of the outer sealing disk edge, the sealing disk has a peripherally extending groove, which is preferably in the cross-sectional shape of the sleeve wall. Preferably, the groove is a circular annular groove. The annular groove diameter preferably corresponds to the sleeve diameter so that the end of a sleeve wall can be inserted, with an open end, into the annular groove of the sealing disk.

Independently of an arrangement with a spring contact element as described hereinbefore, an arrangement with an electrode line connecting socket—without a spring contact element as described hereinbefore—can have a sleeve as described hereinbefore with a seal as described hereinbefore. In that way, electrical contacts in the connecting socket are effectively protected from the ingress of moisture.

The invention also concerns an implantable device with a contact arrangement as described hereinbefore. The implantable device can be a cardiac pacemaker, a cardioverter, a defibrillator or a combination thereof. The electrode line connecting socket is preferably arranged in the header of an implantable device.

BRIEF DESCRIPTION OF THE SEVERAL VIEWS OF THE DRAWINGS

The invention will now be described hereinafter with reference to the Figures in which.

DETAILED DESCRIPTION OF THE INVENTION

Figure 1:
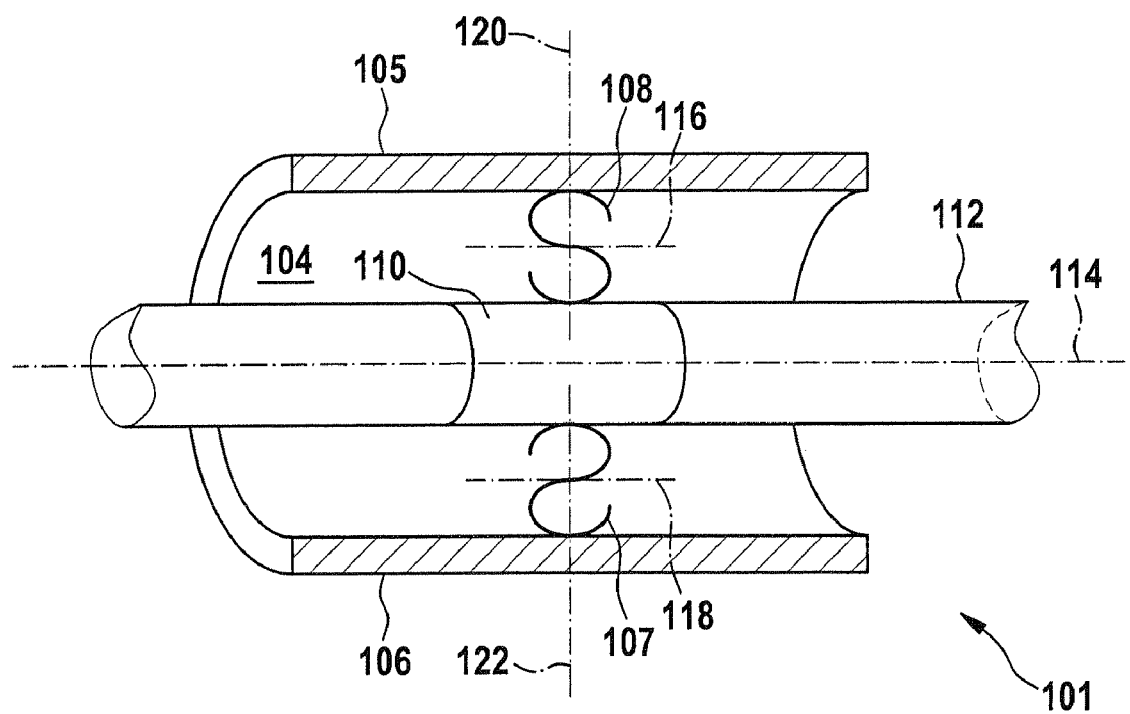
FIG. 1 diagrammatically shows a longitudinal section of an embodiment of an arrangement for an electrode line connecting socket having a sleeve and spring contact elements, FIG. 2a diagrammatically shows a longitudinal section of an arrangement having a sleeve which has spring contact elements and a seal, FIG. 2b diagrammatically shows an exploded view of the arrangement shown in longitudinal section in FIG. 2, and FIGS. 3a and b show an alternative to the variant illustrated in FIG. 2.

FIG. 1 diagrammatically shows a longitudinal section through an arrangement 101 for an electrode line connecting socket of an implantable device.

The arrangement 101 includes a sleeve 105 with a centrally extending sleeve longitudinal axis 114, the sleeve 105 enclosing an internal sleeve space 104.

The sleeve 105 can be arranged in an electrode line socket in such a way that the sleeve longitudinal axis 114 forms a common axis with a socket longitudinal axis or is parallel thereto.

The internal sleeve space 104 is open at each of the ends of the sleeve 105 so that a plug—of which a portion is shown in this Figure—of an electrode line 112 can usually be inserted into the internal sleeve space 104 along the sleeve longitudinal axis 114.

The sleeve 105 includes a sleeve wall 106, wherein spring contact elements 107 and 108 are arranged facing inwardly in a radial direction at the inside of the sleeve wall 106. The spring contact elements 108 and 107 are arranged in the internal sleeve space, to spring in opposite relationship in the radial direction to the sleeve longitudinal axis 114 and thus also the inserted plug of an electrode line 112, which is illustrated in this view.

The spring contact element 107 is formed from a metallic spring tongue and is alternately turned in opposite relationship parallel to a spring transverse axis 118 so that the spring contact element 107 has two turn portions with respectively opposite turn directions. The spring contact element 107 is adapted, with deflection at least along a spring deflection axis 122, to produce a force acting in opposition to the deflection. In this embodiment, the deflection is caused along the spring deflection axis 122 radially outwardly, that is to say in the direction of the sleeve wall 106, by the plug of an electrode line 112, which is inserted along the sleeve longitudinal axis 114, so that the spring contact element 107 is compressed.

The sleeve 105 also includes a spring contact element 108 arranged at the inside of the sleeve wall 106.

The spring contact element 108, just like the spring contact element 107, is formed from a metal spring tongue and also has two turn portions involving respectively opposite turn directions.

The spring contact element 108 is adapted, with deflection along a spring deflection axis 120, to produce a spring force opposing the deflection. The spring deflection axis 120 and the spring transverse axis 116 are mutually orthogonal; the spring deflection axis 122 and the spring transverse axis 116 are also mutually orthogonal.

Figure 2A:
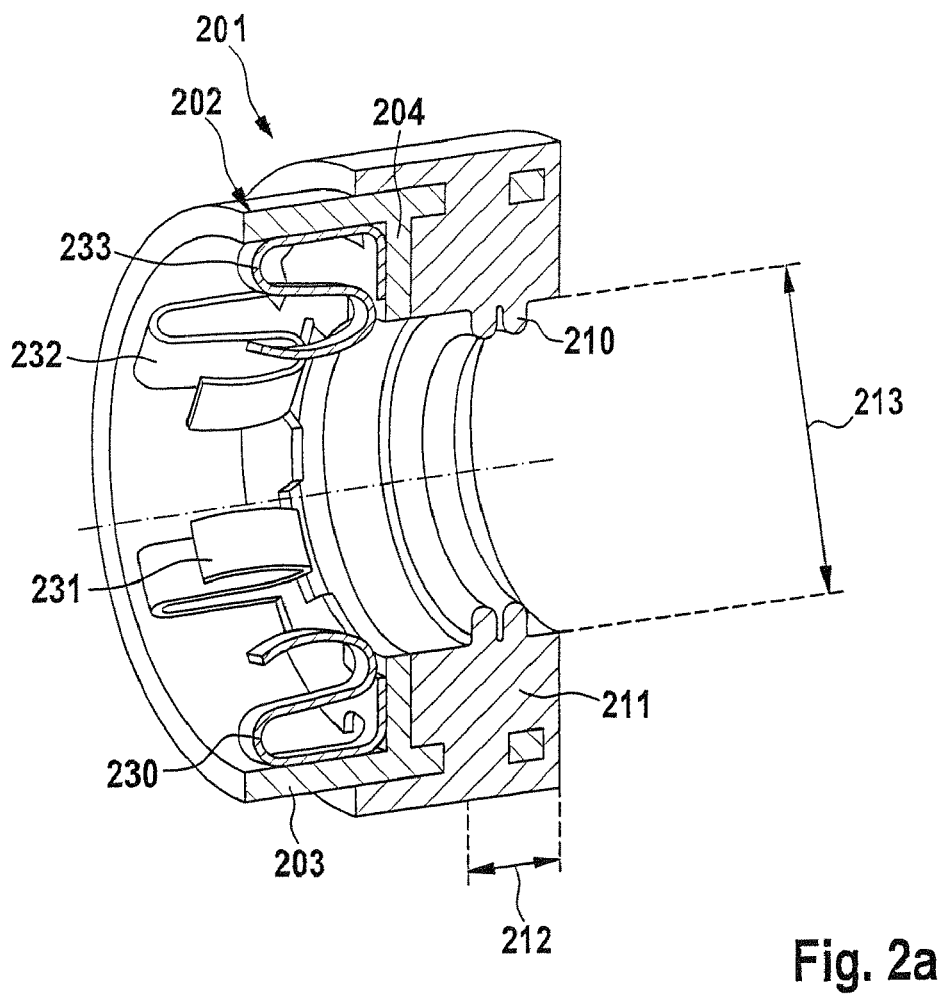

FIG. 2a diagrammatically shows a longitudinal section of a view of an arrangement 201 for an electrode line connecting socket which includes a sleeve 202 with a sleeve wall 203, spring contact elements 230, 231, 232, 233 and a sealing ring 211 of a sealing ring thickness 212. The sealing ring 211 has a round aperture 213 for receiving an electrode line of round cross-section and is so shaped that the sleeve wall is sealed off in relation to the aperture 213.

The sleeve 202 has a separating wall 204 arranged in the internal sleeve space and which divides the internal sleeve space along a sleeve longitudinal axis (not shown in this Figure). The separating wall 204 has a centrally arranged round aperture for passing an electrode line plug therethrough. The diameter of the separating wall aperture corresponds to the diameter of the sealing disk aperture 213.

The sealing disk 211 is of a sealing disk thickness 212 so that the aperture in the sealing disk 211 has an aperture internal wall. The aperture internal wall has two sealing lips 210 arranged in succession in the longitudinal axis of the sleeve. The sealing lips each face radially inwardly and are formed on the sealing disk.

Figure 2B:
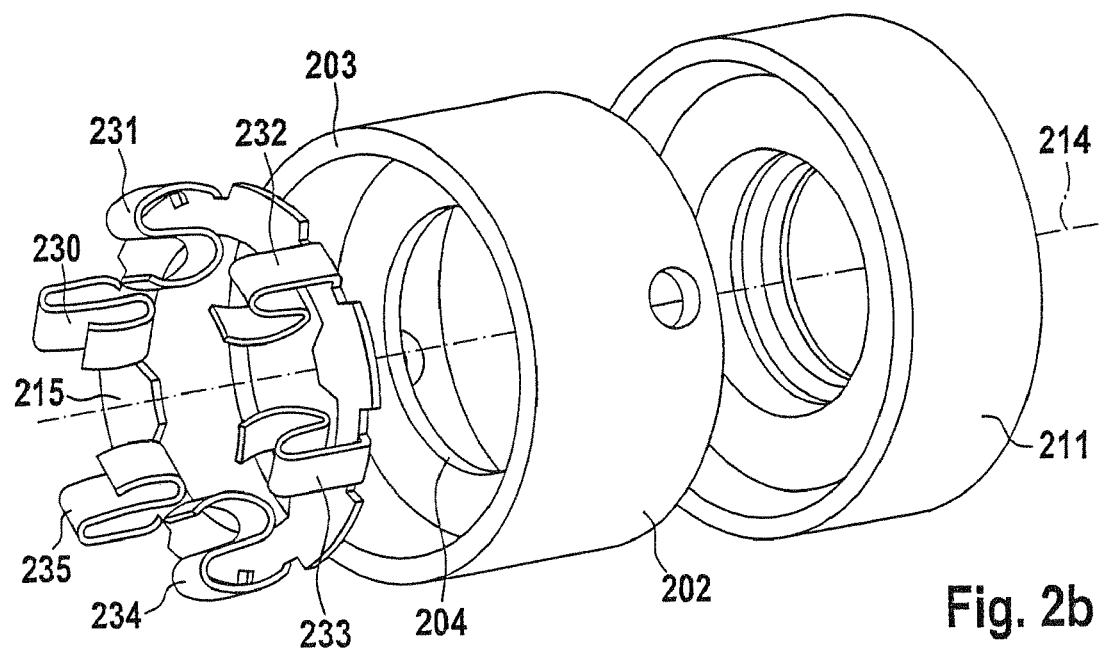

FIG. 2b diagrammatically shows an exploded view of the arrangement illustrated in longitudinal section in FIG. 2a for an electrode line socket. The arrangement for an electrode line socket includes a sleeve 202, a sealing disk 211 and a spring contact element carrier 215 with six spring contact elements 230, 231, 232, 233, 234 and 235 formed thereon.

The sleeve 202 has a sleeve wall 203 which encloses an internal sleeve space. The internal sleeve space is opened along the sleeve longitudinal axis 214 to the sleeve ends at least at one end and in the illustrated embodiment at both ends (end faces).

The sleeve 202 has a separating wall 204 which is arranged in the internal sleeve space and is shaped on the sleeve wall 203. The separating wall 204 has a centrally arranged circular aperture for passing an electrode line plug therethrough, along the sleeve longitudinal axis 204. The separating wall 204 is spaced from the respective sleeve ends in the direction of the sleeve longitudinal axis 204.

The spring contact element carrier 215 is in the form of a circular flat disk having a centrally arranged aperture for an electrode line plug to be passed therethrough.

The spring contact element carrier 215 has six spring contact elements 230, 231, 232, 233, 234 and 235 which are arranged uniformly in the peripheral direction and which are formed at the outer edge of the spring contact element carrier 215.

The spring contact elements are respectively formed from a leaf spring which is turned in a wave shape, wherein the leaf spring has two turn portions each involving opposite turn directions and thus is of an S-shaped wave shape.

The spring contact elements 230, 231, 232, 233, 234 and 235 produced in that way are adapted, upon deflection along the spring deflection axis, to produce a spring force opposing the deflection and—in the situation of use—upon the insertion of an electrode line plug—can deflect resiliently elastically—substantially radially—outwardly.

The spring contact element carrier 215 has recess regions respectively laterally adjoining the spring contact elements in the peripheral direction.

The spring contact element carrier also has in the peripheral direction respective recess regions arranged in opposite relationship to each spring contact element, at the inside edge which adjoins the aperture in the spring contact element carrier.

In this embodiment, the spring contact element carrier 215 and the spring contact elements are stamped out of a metal sheet portion. The spring contact elements are respectively formed from leaf spring strips which face radially outwardly in a radiating configuration and which, to produce the wave shape, are bent over at a right angle at the peripheral attachment of the spring contact element carrier 215 and in their further course are shaped to afford an S-shaped wave shape.

The recesses laterally of the spring contact elements are cut in the radial direction to such a depth that the spring contact element which is bent over at a right angle does not exceed the outer diameter of the spring contact element carrier.

The recesses at the inner edge of the spring contact element carrier 215 towards the aperture are cut outwardly in a radial direction to such a depth that a region of the spring contact element carrier 215, which is still present, between the outer and the inner recesses—as viewed in the radial direction—forms a torsion spring operative in a tangential direction.

The torsion spring formed in that way assists the spring action of the spring contact element in such a manner that the torsion spring acts in series with the spring contact element. The overall spring stiffness resulting therefrom, formed from the spring stiffness of the torsion spring and that of the spring contact element, is less than the spring stiffness of the spring contact element without the torsion spring acting in series.

The spring contact element carrier 215 is of such a dimension in respect of its outside peripheral diameter that it can be inserted into the internal sleeve space along the sleeve longitudinal axis.

The arrangement also includes a sealing disk 211—already described with reference to FIG. 2a-having an annular groove spaced from the outer edge of the sealing disk. The diameter of the annular groove corresponds to the diameter of the sleeve 202 so that an end of the sleeve wall 203 can be inserted in the direction of the sleeve longitudinal axis into the annular groove in the sealing disk 212.

Figure 3A:
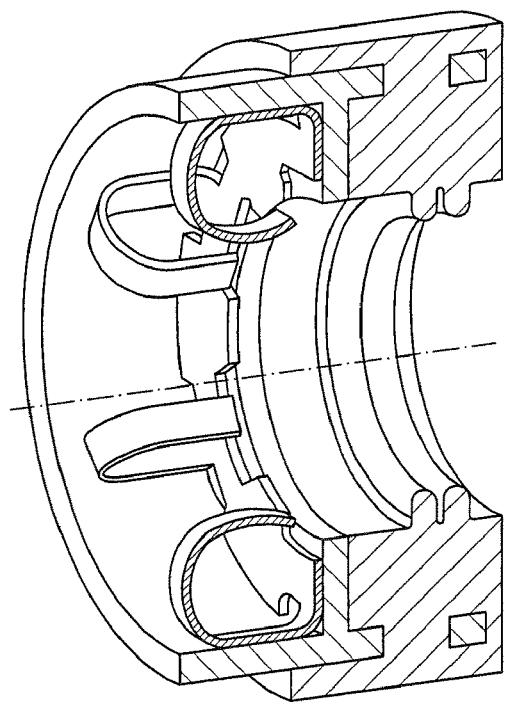
Figure 3B:
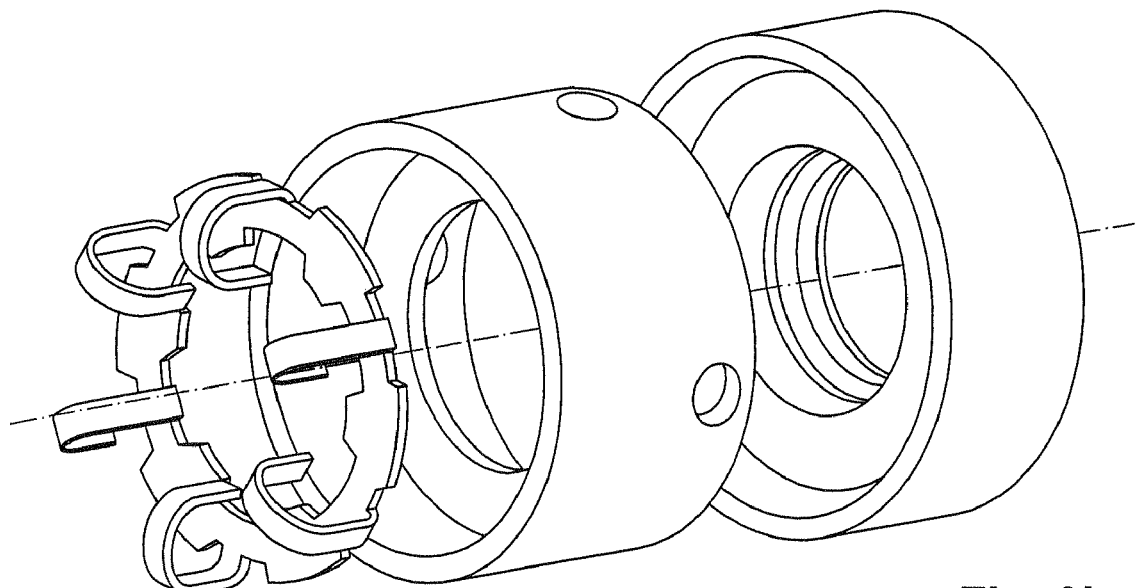

The variant shown in FIGS. 3a and 3b differs from the foregoing description by virtue of the configuration of the spring contact elements. They each have only one turn portion and are C-shaped. The advantageous combination of a sealing disk with a spring contact element carrier having inwardly projecting spring contact elements which are arranged within a common sleeve in the longitudinal direction thereof is equally implemented in both variants.

What is claimed is:

1. A contact arrangement for connecting an electrode line to an implantable device, comprising
   an electrical connecting socket configured for the implantable device with a socket longitudinal axis and at least one opening for the insertion of a plug along the socket longitudinal axis,
   at least one electrically conductive spring contact element which is arranged and adapted to deflect resiliently elastically outwardly upon insertion of a plug, in that case to be compressed at least in a spring deflection direction extending transversely with respect to the socket longitudinal axis and to provide a spring force acting in opposition to the compression,
   wherein
   the spring contact element has an integral metallic spring contact tongue with a socket spring contact tongue portion and a plug spring contact tongue portion which extend transversely with respect to the spring deflection direction and which are connected together by turn portions, wherein turn portions which occur in immediate succession in the spring deflection direction are turned towards each other with respectively opposite turn directions with the socket spring contact tongue portion and the plug spring contact tongue portion extending from the turn portions in opposite directions, and wherein the socket spring contact tongue portion and the plug spring contact tongue portion are compressed toward each other upon deflection.

2. A contact arrangement as set forth in claim 1, wherein the spring contact tongue is turned in such a way that in a plan view on to a plane defined by the socket longitudinal axis and the spring deflection direction, the spring contact tongue is of a wave shape.

3. A contact arrangement as set forth in claim 2, wherein the wave shape is an S-shaped or a rectangular or a triangular wave shape.

4. A contact arrangement as set forth in claim 1, wherein the spring contact element has three or four turn portions.

5. A contact arrangement as set forth in claim 1, wherein the spring contact tongue of the spring contact element is a turned leaf spring with a leaf spring cross-sectional profile, wherein the width dimension of the leaf spring cross-sectional profile is greater than the height dimension of the leaf spring cross-sectional profile.

6. A contact arrangement as set forth in claim 5, wherein the spring contact element has at least one elastomer element which at least partially fills an intermediate space which extends between two leaf spring portions disposed in opposite relationship in the radial direction, and wherein the elastomer element is designed and arranged to limit deflection travel of the spring contact element.

7. A contact arrangement as set forth in claim 1, comprising at least three spring contact elements wherein the spring deflection directions of the spring contact elements are arranged on a common plane extending perpendicularly to the socket longitudinal axis.

8. A contact arrangement as set forth in claim 1, wherein a contact portion of the spring contact tongue has a surface region which is provided for making contact with a counterpart contact of an electrode line plug and which is convexly shaped.

9. A contact arrangement as set forth in claim 1, wherein the arrangement has a sleeve with a sleeve longitudinal axis and a sleeve wall, wherein
   the sleeve wall encloses an internal sleeve space having at least one opening for receiving an electrode plug in the direction of the sleeve longitudinal axis,
   and wherein the sleeve longitudinal axis and the socket longitudinal axis are mutually parallel and the spring contact element is at least partially arranged in the internal sleeve space.

10. An implantable device having a contact arrangement as set forth in claim 1, wherein the implantable device is a cardiac pacemaker, a cardioverter, a defibrillator or a combination of same.

* * * * *

UNITED STATES PATENT AND TRADEMARK OFFICE
CERTIFICATE OF CORRECTION

| | |
|---|---|
| PATENT NO. | : 7,587,244 B2 |
| APPLICATION NO. | : 11/099064 |
| DATED | : September 8, 2009 |
| INVENTOR(S) | : Ralf et al. |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 448 days Delete the phrase "by 448 days" and insert -- by 653 days --

Signed and Sealed this

Twenty-fourth Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,587,244 B2 | Page 1 of 1 |
| APPLICATION NO. | : 11/099064 | |
| DATED | : September 8, 2009 | |
| INVENTOR(S) | : Ralf Olbertz | |

It is certified that error appears in the above-identified patent and that said Letters Patent is hereby corrected as shown below:

Title Page

Item 73 reads "Biotronik GmbH & Co. KG (DE)".

should read "Biotronik CRM Patent AG (CH)".

Signed and Sealed this

Second Day of November, 2010

David J. Kappos
*Director of the United States Patent and Trademark Office*